United States Patent
Boyle et al.

(10) Patent No.: US 10,514,361 B2
(45) Date of Patent: Dec. 24, 2019

(54) TATTLETALE ION-IMPLANTED NANOPARTICLES

(71) Applicants: National Technology & Engineering Solutions of Sandia, LLC, Albuquerque, NM (US); STC.UNM, Albuquerque, NM (US)

(72) Inventors: Timothy J. Boyle, Albuquerque, NM (US); Khalid Mikhiel Hattar, Albuquerque, NM (US); Fernando Henry Garzon, Santa Fe, NM (US); Stephen J. Bauer, Albuquerque, NM (US)

(73) Assignees: National Technology & Engineering Solutions of Sandia, LLC, Albuquerque, NM (US); STC.UNM, Albuquerque, NM (US)

( * ) Notice: Subject to any disclaimer, the term of this patent is extended or adjusted under 35 U.S.C. 154(b) by 0 days.

(21) Appl. No.: 16/107,792

(22) Filed: Aug. 21, 2018

(65) Prior Publication Data
US 2019/0064111 A1 Feb. 28, 2019

Related U.S. Application Data

(60) Provisional application No. 62/551,336, filed on Aug. 29, 2017.

(51) Int. Cl.
G01N 27/62 (2006.01)
H01J 37/08 (2006.01)
G01K 3/00 (2006.01)
B82Y 40/00 (2011.01)
C04B 41/00 (2006.01)
B82Y 15/00 (2011.01)

(52) U.S. Cl.
CPC ............ *G01N 27/622* (2013.01); *G01K 3/00* (2013.01); *H01J 37/08* (2013.01); *B82Y 15/00* (2013.01); *B82Y 40/00* (2013.01); *C04B 41/0027* (2013.01); *C04B 2235/3218* (2013.01); *C04B 2235/3225* (2013.01); *C04B 2235/3229* (2013.01); *H01J 2237/31701* (2013.01)

(58) Field of Classification Search
USPC ........................................ 250/286
See application file for complete search history.

(56) References Cited

U.S. PATENT DOCUMENTS

| 4,454,233 A * | 6/1984 | Wang | G01N 33/532 436/525 |
|---|---|---|---|
| 7,229,690 B2 * | 6/2007 | Chan | B01J 13/02 428/403 |
| 9,202,600 B2 * | 12/2015 | Ravn | G21G 1/001 |
| 2017/0354601 A1 * | 12/2017 | Niu | A61F 7/00 |

* cited by examiner

*Primary Examiner* — Phillip A Johnston
(74) *Attorney, Agent, or Firm* — Kevin W. Bieg

(57) ABSTRACT

Ion-doped metal or ceramic nanoparticles can be added into, for example, a component that upon exposure to an environmental stimulus, will release the ion and 'tattle' on any impending destruction.

17 Claims, 6 Drawing Sheets

TATTLETALE ION-IMPLANTED NANOPARTICLES

CROSS-REFERENCE TO RELATED APPLICATION

This application claims the benefit of U.S. Provisional Application No. 62/551,336, filed Aug. 29, 2017, which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to non-destructive testing and, in particular, to ion-implanted nanoparticles that release the implanted ions in response to a stimulus.

BACKGROUND OF THE INVENTION

When possible, non-destructive testing (NDT) techniques like radiographic analysis, ultrasonic testing, and magnetic particle inspection can be used for detection but these methods are time-consuming and costly.

SUMMARY OF THE INVENTION

The present invention is directed to ion-doped nanoparticles that can be added into, for example, a component that upon exposure to an environmental stimulus, will release the ion and 'tattle' on any impending destruction. As examples of the invention, three ceramic nanoparticles (CNPs), beohmite (Al(O)OH), yttria ($Y_2O_3$), and ceria ($CeO_2$), were synthesized and pressed into pellets (abbreviated as Al-pellet, Y-pellet, Ce-pellet, respectively). These pellets were ion implanted with 300 keV Kr at 1 $e^{15}$ and 1 $e^{16}$ ions/cm$^2$, which turned the pellets black due to the formation of oxygen vacancies. The Kr was readily detected by a handheld XRF instrument in each pellet. Thermal treatment revealed the ions could be released from the Al-pellet between 800-1600° C., from the Y-pellet at 440° C., and from the Ce-pellet at <1600° C. The release occurs at different temperatures for the three materials, which indicates the pellets can have different thermal 'tattletales' as well. Therefore, the diffusional properties of the materials can be tailored to release the gases at pre-established temperatures, thus providing evidence of thermal events.

In general, the nanoparticle can be a metal or ceramic nanoparticle. Any ion that can be implanted and released in response to a stimulus can be used. Preferably, the implanted ion comprises a noble gas, such as helium, neon, argon, xenon, or krypton, but can also be any gas that can be ionized, such as nitrogen or oxygen. Indeed, the implanted ion can be a reactive ion dopant or controlled ion alloy. The stimulus can be a physical stimulus, such as temperature, pressure, or mechanical crushing or breakage, fatigue, or radiation, or a chemical stimulus, such as corrosion.

For example, ion-implanted, oxide-dispersion-strengthened (ODS) metals can be used as 'tattle-tales' to determine the 'state-of-health' for materials, where harsh environmental situations limit direct-inspection but early defect detection is critical. Uses of this ODS steel range through a variety of devices. For example, making a part out of a "self-monitoring" material can be applied to situations in which environmental/performance loads (corrosion, fatigue, radiation effects) can cause materials deterioration.

BRIEF DESCRIPTION OF THE DRAWINGS

The detailed description will refer to the following drawings, wherein like elements are referred to by like numbers.

FIG. 3($b$) is an MS scan for a Y-pellet without Kr-implantation.

DETAILED DESCRIPTION OF THE INVENTION

Figure 1:
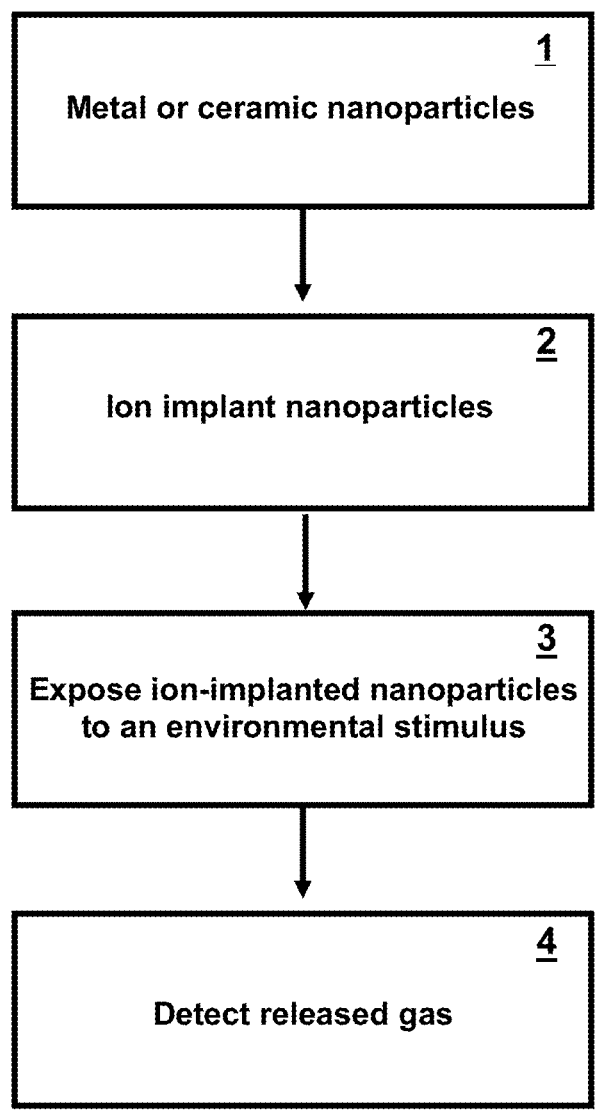
FIG. 1 is a chart showing the method of the present invention.

According to the present invention, ion-implantation can be used to imbed trace ions into nanomaterials. FIG. 1 shows the method of the present invention, comprising providing metal or ceramic nanoparticles, ion-implanting the nanoparticles, exposing the ion-implanted nanoparticles to an environmental stimulus, and detected the gas released from the ion-implanted nanoparticles in response to the stimulus. The release of the implanted (tattletale) gases can be quantitatively detected real-time using nondestructive analysis, for example by using a benchtop focused-beam X-ray fluorescence spectrometer (XRFS) and a quadrupole mass spectrometer. The retained implanted particles can be identified by the same benchtop focused beam XRFS. Sublimation pumped mass spectroscopy can be used to improve the detection limits of the tattletale gas. Measurements can be made in vacuum or by point detection technology in "air".

Determining the optimal factors, such as size, morphological variants, compositions, and level of doping necessary for detection ensures a meta-stable ion-implanted nanoparticle that will properly emit the gas and enable the use of these 'tattle-tale' particulates to passively monitor the health of components comprising the nanoparticles. To determine these factors, a series of CNPs were generated and then ion implanted. Three types of CNPs were produced: a main group ceramic (Al(O)OH), a simple early transition metal oxide ($Y_2O_3$), and a lanthanide oxide ($CeO_2$). These were chosen to represent different species from across the periodic table with a variety of cation sizes. The ion-implanted CNPs were then thermally tested to determine if the CNPs retained the implant. The proper particle size that enables a high level of ion-implantation/expulsion was evaluated.

Ceramic Nanoparticle Preparation

For all the CNP preparations, inert atmosphere techniques were used unless otherwise noted. All chemical precursors described were commercially available. For all three systems, the desired phase and nanomaterials were isolated. These were verified by transmission electron microscopy (TEM) and powder X-ray diffraction (PXRD).

Al(O)OH nanoparticle preparation: Boehmite was synthesized using a hydrothermal method solution precipitation reaction method by placing [Al(OPr$^i$)$_3$]$_4$ in deionized water.

The reaction was heated to reflux for over 24 hours, centrifuged at 3000 rpm, washed with deionized water, and collected in methanol. The methanol solution was then slowly evaporated. TEM images and PXRD patterns confirmed nanoparticles had been isolated.

$Y_2O_3$ nanoparticle preparation: A solution of $Y(NO_3)*6H_2O$ in oleylamine was heated to 350° C. for 1 h. After this time, the insoluble fraction was isolated by centrifugation, washed 3 times with hexanes (Hex) and methanol (MeOH). TEM and PXRD patterns confirmed nanoparticles had been isolated.

$CeO_2$ nanoparticle preparation: A solution of $CeCl_3*6H_2O$ in a mixture of 5 M KOH (5 mL) and toluene (35 mL) was heated to 180° C. for 24 h in a digestion bomb. After this time, the insoluble fraction was isolated by centrifugation, washed 2 times with water and ethanol. This product was heated to 800° C. for 3 h in air. TEM and PXRD patterns confirmed nanoparticles had been isolated.

Once each of the above nanomaterials were synthesized and confirmed by PXRD, TEM grids were loaded for ion implantation. Pellets of these nanoparticles were also prepared. All of the pellets were prepared in a similar manner. The pellets were formed by loading a die with the desired particles. Approximately 0.5 g of the respective nanoparticles were loaded in a ½-inch punch and die, that was placed in the center of a press. The samples were pressed until a pellet was retained upon release. Each sample was pressed to ~3000 tons and kept there for five minutes. Subsequently, the pressure was released and the samples were collected.

Ion Implantation

Pellets of all three compositions were implanted using a 350 kV ion implanter with 300 keV Kr into pellets at $1\ e^{15}$ and $1\ e^{16}$ ions/cm². The ion beam was rastered over the pellets through a larger non-contact mask to provide the most uniform dose distribution. During Kr implantation at various energies, significant changes in the optical properties of the pellets were observed. Optical images of the pellets after ion implantation revealed darkening of the sample. This is believed to be due to the creation of oxygen vacancies. The color is lost upon heating, suggesting the color centers were annealed out of the implanted nanostructure.

Nanoparticles of all three compositions were implanted at 10 keV He to determine the defect structures formed from noble gas implantation. Nanoparticles of all three compositions were prepared on standard transmission electron microscope (TEM) grids (carbon film on copper grids). The samples were than implanted with a broad beam of 10 keV He using a 10 kV Colutron accelerator. A broad beam was utilized to implant one sample of each composition to doses of $1\ e^{14}$, $1\ e^{16}$, and $1\ e^{17}$. This technique provides for a rapid method to characterize the defect type and structure in the nanoparticles from noble gas implantation.

The presence of the ion implantation in the pellets and nanoparticles was determined using XRF analyses. Samples were analyzed using a XRF instrument, with a Rh target, 45 KeV, 0.8-1 mA beam current, and silicon drift detector (SDD). A Ni filter was used to enhance selective excitation. The Kr $K_{alpha}$ peak was used for analysis. Data were collected until the peak intensities were more than 3 sigmas above background. Elemental concentration quantification was performed using the EDAX Fundamental Parameters Quantification program. For each ion-implanted sample, Kr was detected. XRF analyses indicated that the surface that had been ion implanted with Kr was stable and could be detected several days after the implantation. It is of note that Kr could be detected only on the surface that had been ion implanted. That is, the ion could not be detected through the back of the pellet.

Implanted Ion Release

Thermal treatment was performed to demonstrate release of the implanted ions. These tests demonstrated that the 'tattletales' could survive processing and would give up the Kr ion upon thermal sitmulus.

Three Kr-implanted CNPs (alumina, yttria, and ceria) and one control sample (yttria NP without Kr-implantation) were characterized in a thermogravimetric analyzer/differential scanning calorimeter (TGA/DSC) with simultaneous off-gas speciation via mass spectrometry (MS). Specimens were loaded into alumina cups and heated at a rate of 50° C. $min^{-1}$ from 25 to 1570° C., then held isothermally at 1570° C. for 30 minutes, all under a flow of 60 ml $min^{-1}$ UHP argon.

Figure 2A:
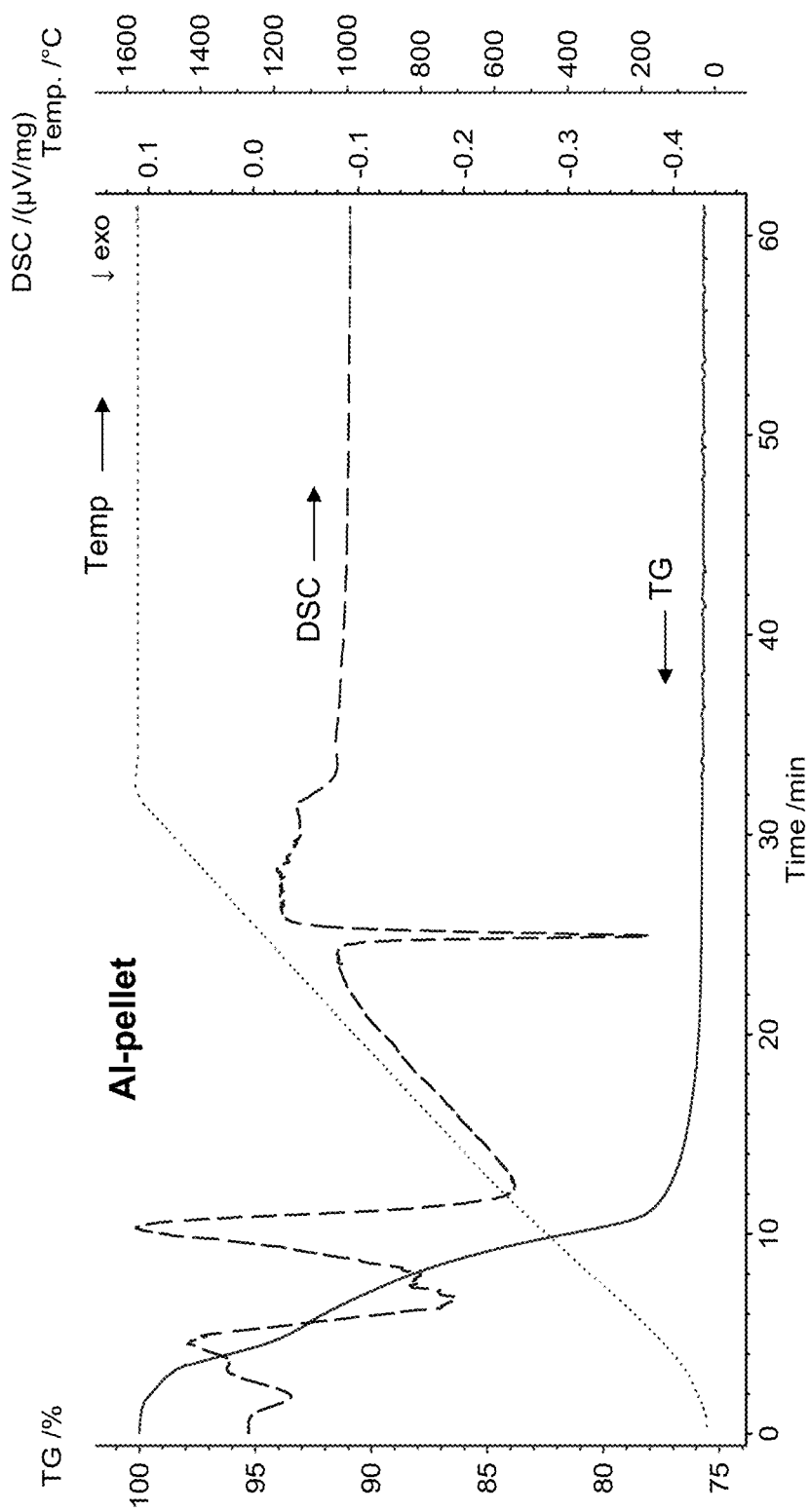
FIGS. 2($a$)-($c$) are thermogravimetric analyzer/differential scanning calorimeter (TGA/DSC) scans of an ion-implanted Al-pellet, Y-pellet, and Ce-pellet, respectively.
Figure 2B:
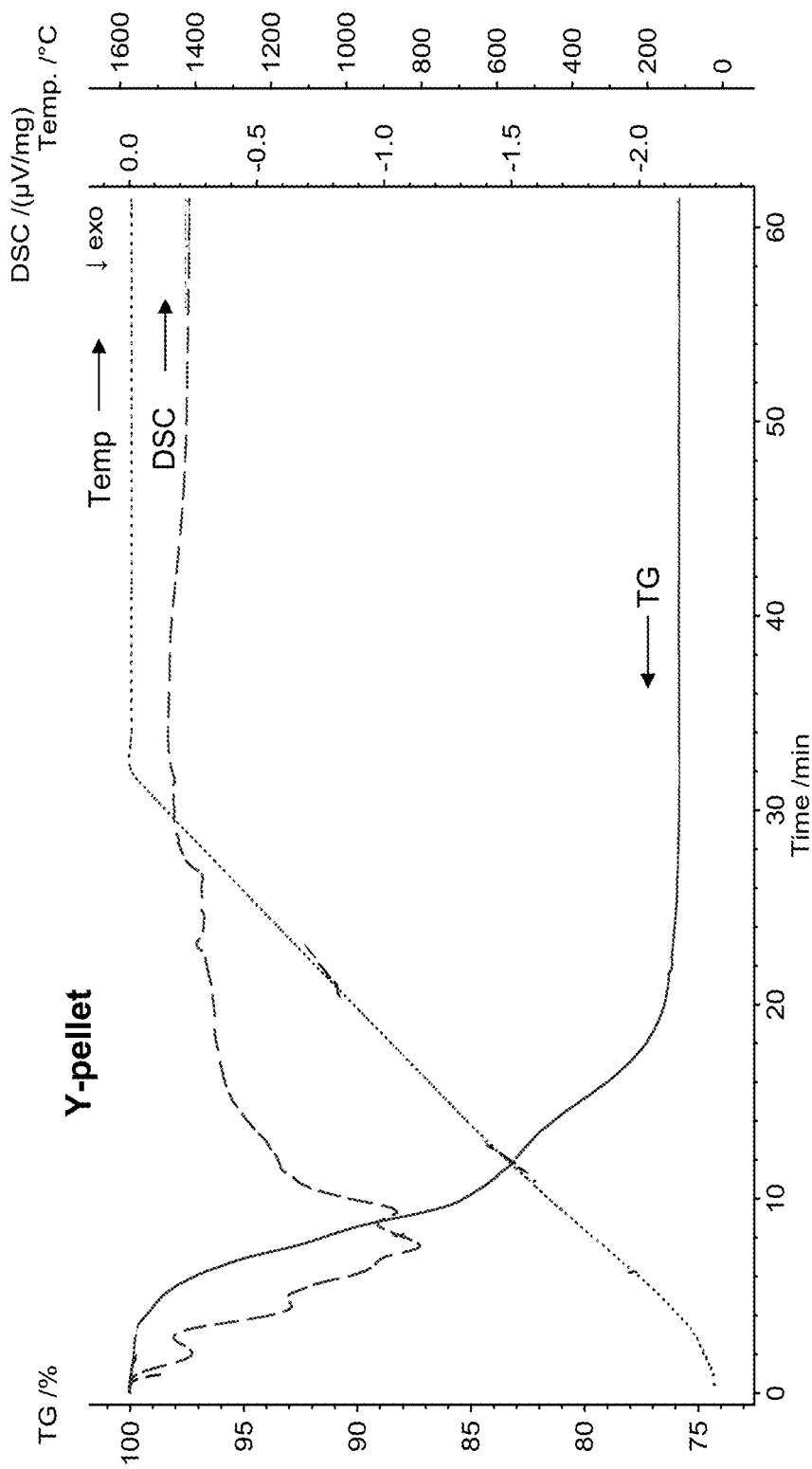
Figure 2C:
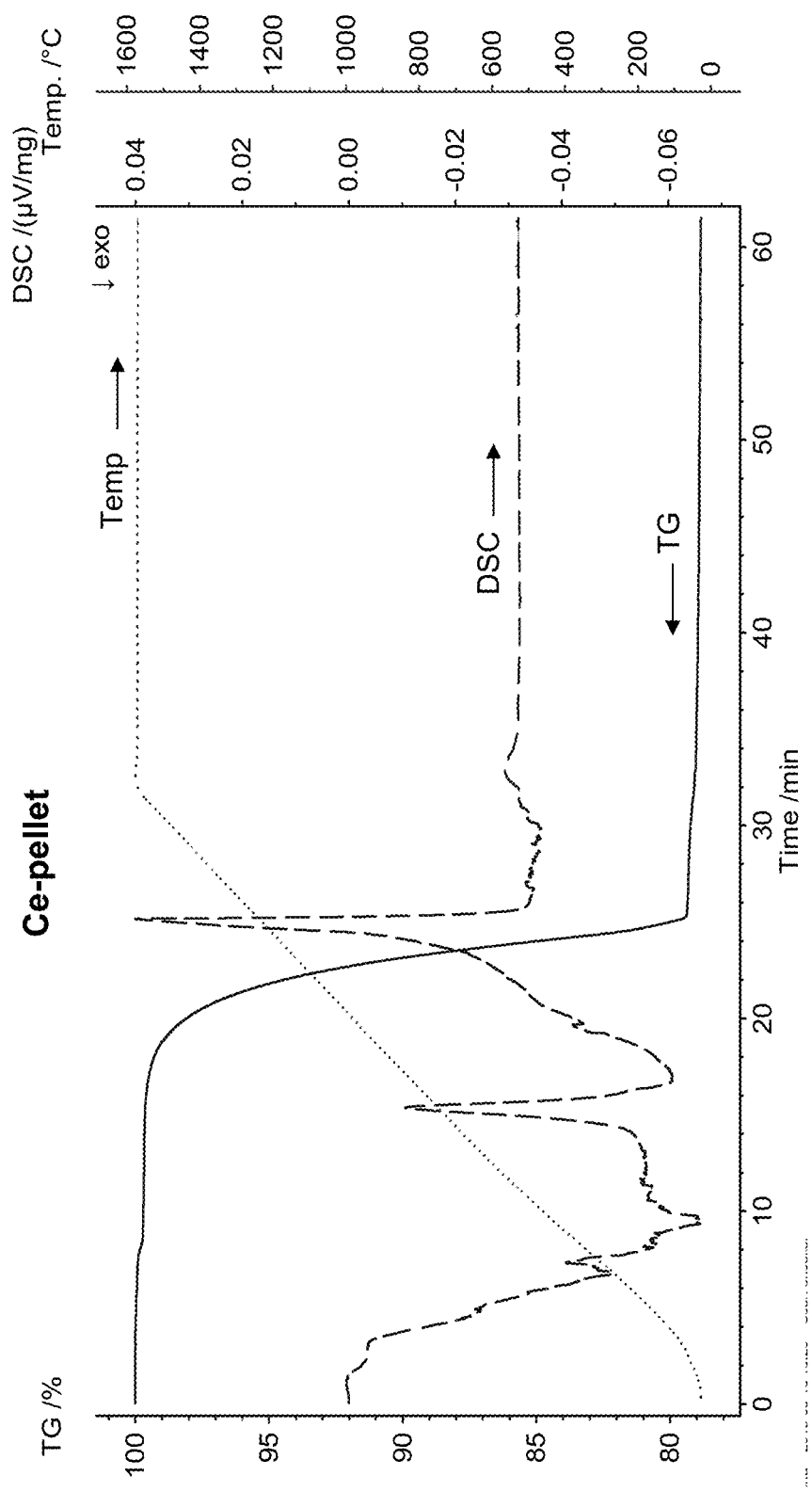
Figure 3A:
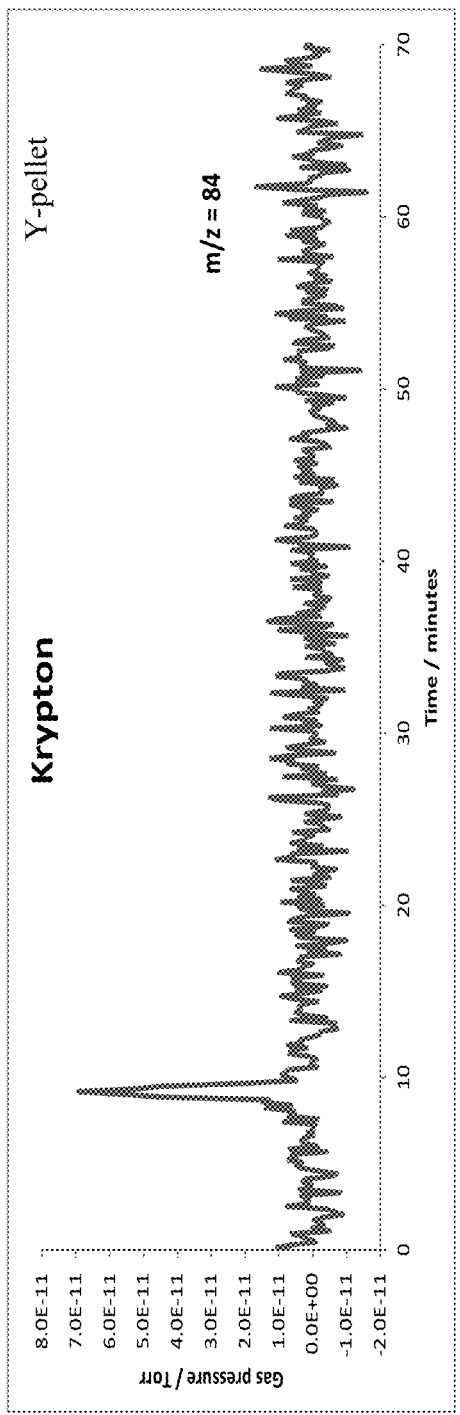
FIG. 3($a$) is mass spectrometer (MS) scan at mass/charge=84 for a Kr-implanted Y-pellet heated up to 1570° C.
Figure 3B:
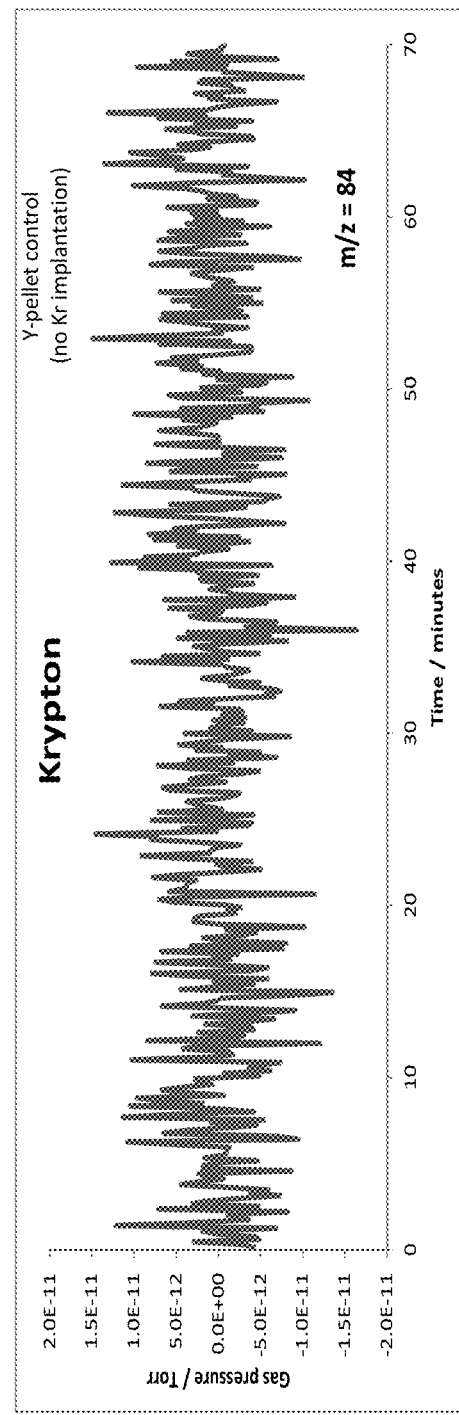
Figure 4:
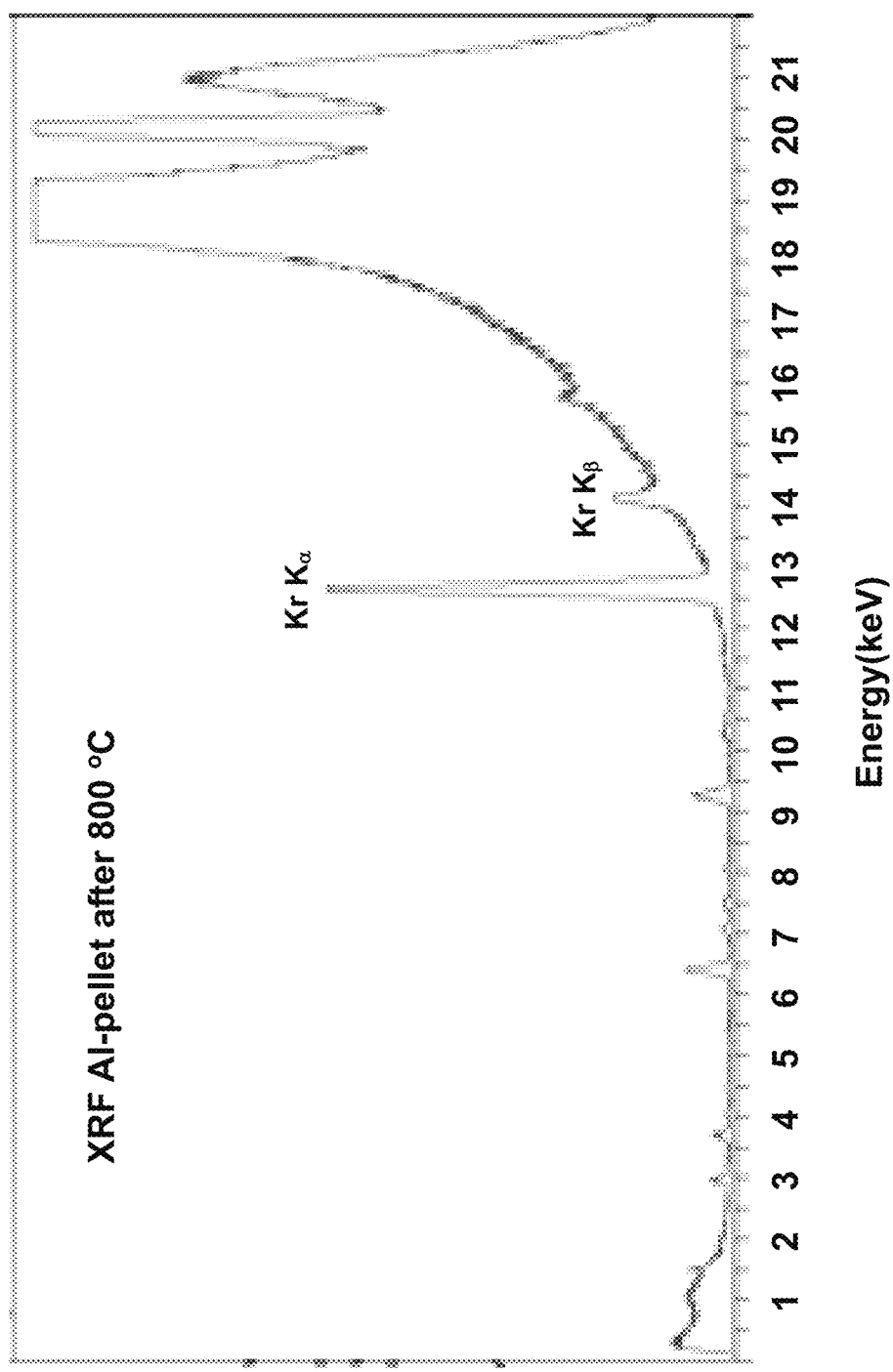
FIG. 4 is an X-ray fluorescence (XRF) scan of an Al-pellet heated to 800° C.

All three CNPs showed marked mass losses during heating due to condensation of their respective oxide structures and possible evolution of volatile species, as shown in FIGS. 2(a)-(c). The Kr-implanted yttria CNP showed a peak in the MS at mass/charge=84 at 9.5 minutes into the run (temperature ca. 440° C.), as shown in FIG. 3(a). It was verified that this peak was not due to other off-gassing species with mass 84 by running a control experiment (identical sample preparation, but without Kr-implantation), as shown in FIG. 3(b). XRF analyses of the Al-pellet revealed Kr present after 800° C., as shown in FIG. 4, but not after 1570° C. treatment. All other pellets did not have Kr present after thermal treatment.

The present invention has been described as tattletale ion-implanted nanoparticles. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A tattletale nanoparticle, comprising an ion-implanted nanoparticle that releases the implanted ion in response to a stimulus, and detecting the released implanted ions.

2. The tattletale nanoparticle of claim 1, wherein the nanoparticle is implanted to a dose, of greater than $1\ e^{15}$ ions/cm².

3. The tattletale nanoparticle of claim 1, wherein the nanoparticle comprises a ceramic nanoparticle.

4. The tattletale nanoparticle of claim 3, wherein the ceramic nanoparticle comprises beohmite, yttria, or ceria.

5. The tattletale nanoparticle of claim 1, wherein the nanoparticle comprises a metal nanoparticle.

6. The tattletale nanoparticle of claim 1, wherein the implanted ion comprises a noble gas.

7. The tattletale nanoparticle of claim 1, wherein the implanted ion comprises an ionizable gas.

8. The tattletale nanoparticle of claim 1, wherein the implanted ion comprises a reactive dopant or controlled ion alloy.

9. The tattletale nanoparticle of claim 1, wherein the stimulus comprises a physical stimulus.

10. The tattletale nanoparticle of claim 9, wherein the physical stimulus comprises heating the nanoparticle to above a release temperature.

11. The tattletale nanoparticle of claim 9, wherein the physical stimulus comprises mechanical crushing.

12. The tattletale nanoparticle of claim 1, wherein the stimulus comprises a chemical stimulus.

13. A method for non-destructive testing, comprising:
   providing a plurality of ion-implanted metal or ceramic nanoparticles in a component under test,
   exposing the component to an environmental stimulus, thereby causing the implanted ion to be released in response to the environmental stimulus, and
   detecting the released implanted ions.

14. The method of claim 13, wherein the environmental stimulus comprises a physical stimulus.

15. The method of claim 13, wherein the environmental stimulus comprises a chemical stimulus.

16. The method of claim 13, wherein the released implanted ions are detected with a mass spectrometer.

17. The method of claim 16, wherein the mass spectrometer comprises a sublimation pumped mass spectrometer.

* * * * *